US00RE36175E

United States Patent [19]

Shaner

[11] E Patent Number: Re. 36,175

[45] Reissued Date of Patent: Mar. 30, 1999

[54] METHODS FOR DETECTING ACETOHYDROXYACID SYNTHASE INHIBITORS

[75] Inventor: Dale L. Shaner, Lawrenceville, N.J.

[73] Assignee: American Cyanamid Company, Madison, N.J.

[21] Appl. No.: 692,059

[22] Filed: Aug. 5, 1996

Related U.S. Patent Documents

Reissue of:

[64] Patent No.: 5,356,789
Issued: Oct. 18, 1994
Appl. No.: 68,458
Filed: May 28, 1993

[51] Int. Cl.[6] ..... C12Q 1/26; C12N 9/02

[52] U.S. Cl. ..... 435/25; 435/69.2; 435/189; 436/128; 436/129; 436/131; 504/116; 504/130; 504/148; 504/225; 504/273

[58] Field of Search ..... 435/25, 69.2, 189; 436/128, 129, 131; 504/116, 130, 148, 225, 273

[56] References Cited

U.S. PATENT DOCUMENTS

| | | | |
|---|---|---|---|
| 4,127,405 | 11/1978 | Levitt | 71/93 |
| 4,380,656 | 4/1983 | Fayter | 549/473 |
| 4,517,763 | 5/1985 | Beversdorf | 47/58 |
| 4,545,146 | 10/1985 | Davis | 47/58 |
| 4,547,218 | 10/1985 | Malhotra et al. | 71/94 |
| 4,586,949 | 5/1986 | Gerwick | 71/91 |
| 4,648,204 | 3/1987 | Davis | 47/58 |
| 4,699,649 | 10/1987 | Rorer | 71/90 |
| 4,701,208 | 10/1987 | Los | 546/15 |
| 4,761,373 | 8/1988 | Anderson | 435/172 |
| 4,954,163 | 9/1990 | Kleschek | 71/92 |
| 5,010,195 | 4/1991 | Van Heertum et al. | 544/263 |
| 5,084,082 | 1/1992 | Sebastian | 71/90 |
| 5,084,083 | 1/1992 | Lewis | 71/90 |
| 5,084,086 | 1/1992 | Forney et al. | 544/321 |
| 5,102,447 | 4/1992 | Gates | 514/127 |
| 5,163,995 | 11/1992 | Van Heertum et al. | 71/92 |
| 5,187,071 | 2/1993 | Fischer et al. | 435/32 |
| 5,206,135 | 4/1993 | Abell et al. | 435/4 |
| 5,231,020 | 7/1993 | Jorgensen et al. | 435/172 |
| 5,292,937 | 3/1994 | Manning et al. | 562/457 |

FOREIGN PATENT DOCUMENTS

| | | | |
|---|---|---|---|
| WO8705898 | 10/1987 | WIPO | 106/36 |

OTHER PUBLICATIONS

Slatz and Raborg, 150 J. Biol. Chem., 25 (1943).

Westerfield, A Calorimetric Determination of Blood Acetoin, 161 J. Biol. Chem., 495–502 (1945).

Miflin, Cooperative Feedback of Barley Acetohydroxyacid Synthetase by Leucine, Isoleucine, and Valine, 146 Archives of Biochemistry and Biophysics 542–550 (1971).

Schloss, Interaction of the Herbicide Sulfometuron Methyl With Acetolactate Synthase: A Slow–Binding Inhibitor, Flavins and Flavoproteins, 737–740 (ed. Bray et al. 1984).

Kionka and Amrhein, The enzymatic malonylation of 1–aminocyclopropane–1–carboxylic acid in homogenates of mung–bean hypocotyls, 162 Planta 226–235 (1984).

Shaner, et al., Imidazolinones: Potent Inhibitors of Acetohydroxyacid Synthase, 76 Plant Physiol. 545–546 (1984).

Schloss, Origin of The herbicide binding site of acetolactate synthase, 331 Nature 360–362 (1988).

Schloss and Aulabaugh, Acetolactate synthase and keto-l–acid reductoismerase: A search for reason and a reason for search, Proceedings Of The Workshop On The Biosynthesis Of Branched Chain Amino Acids, 329–356 (ed. Barak et al. 1988).

Schultz, et al., The herbicidally active experimental compound Hoe 704 is a potent inhibitor of the enzyme acetolactate reductoisomenase, 238 FEBS Letters 375–378 (1988).

Singh, et al. Assay of Acetohydroxy Acid Synthase, 171 Analytical Biochemistry 173–179 (1988).

Subramanian and Gerwick, Inhibition of Acetolactate Synthase By Triazolopyrimidines, Biocatalysis in Agricultural Biotechnology, Chap. 19, 277–288 (ed. Whitaker et al. 1989).

Subramanian, et al., Mechanism of Action of 1,2,4–Treazolo [1,5–a]Pyrimidine Sulfonamide Herbicides, 1989 BCPC Mono. No. 42 Amino Acid Biosynthesis Inhibitors 97–101 (1989.

Chunduru, et al., Mechanism of Ketol Acid Reductiosomerase—Steady–State Analysis and Metal Ion Requirement, 28 Biochemistry 486–493 (1989).

Subramanian, et al., Properties of Mutant Acetolactate Synthases Resistant to Triazolopyrimidine Sulfonailide, 94 Plant Physiol. 239–244 (1990).

de Castro and Youmans, Whole Plant Studies on Weed Resistance to ALS/AHAS Inhibiting Herbicides, 43 Western Society of Weed Science 79–80 (1990).

Gerwick, et al., Mechanism of Action of the 1,2,4–Triazolo [1,5–a]pyrimidines, 29 Pestic. Sci. 357–364 (1990).

Shaner, et al., Interaction of Imidazolinones with Plant Acetohydroxy Acid Synthase: Evidence for In Vivo Binding and Competition with Sulfometuron Methyl, 38 J. Agric. Food Chem. 1279–1283 (1990).

Epelbaum, et al., Determination of Products of Acetohydroxy Acid Synthase by the Colorimetric Method, Revisited, 191 Analytical Biochemistry 96–99 (1990).

Aulabaugh and Schloss, Oxalyl Hydroxamates as Reaction–Intermediate Analogous for Ketol–Acid Reductoisomerase, 29 Biochemistry 2824–2830 (1990).

(List continued on next page.)

*Primary Examiner*—Louise N. Leary
*Attorney, Agent, or Firm*—Charles F. Costello, Jr.

[57] ABSTRACT

The invention provides a method for determining whether a compound inhibits acetohydroxyacid synthase. The invention further provides a method for determining whether a plant is resistant to an acetohydroxyacid synthase inhibiting compound.

45 Claims, No Drawings

OTHER PUBLICATIONS

Shaner, Mechanism of Resistance to Acetolactate Synthase/ Acetohydroxyacid Synthase Inhibitors, Herbicide Resistance in Weeds and Crops 187–198 (ed. Caseley et al. 1991).
Subramanian, et al., Acetolactate Synthase Inhibiting Herbicides Bind to the Regulatory Site, 96 Plant Physiol. 310–313 (1991).
Stidham, Herbicidal inhibitors of branched chain amino acid biosynthesis, Herbicides 247–266 (ed. Baker et al. 1991).
Wittenback, et al. Pressure Points in the Biosynthetic Pathway for Branched–Chain Amino Acids, in Biosynthesis and Molecular Regulation of Amino Acids in Plants 69–88 (ed. Singh et al. (1990).
Mourad and King, Effect of four classes of herbicides in growth and acetolactate–synthase activity in several variants of *Arabidopsis thaliana,* 188 Planta 491–497 (1992).
Kleschick, et al. 1,2,4–Triazolo[1,5–a] pyrimidine–2–sulfonanilide herbicides, Synthesis and Chemistry of Agro Chemicals III Chaps. 2 and 3, 10–24 (Am. Chem. Soc. 1992).
Costales, et al. Synthasis and Herbicidal Activity of N–(Substituted–2–Fluorophenyl)–1,2,4–Triazolo–[1,5a]–Pyrimidine Sulfonamides, Synthesis and Chemistry of Agro Chemicals III (Am. Chem. Soc. 1992).
Yamamoto et al. Synthesis of NC–319: A New Sulfonylurea in Corn, Synthesis and Chemistry of Agro Chemicals III (Am. Chem. Soc. 1992).
Gerwick, et al., Rapid Diagnosis of ALS/AHAS–Resistant Weeds, 7 Weed Technology 519–524 (1993).
Bernasconi, et al., Functional Expression of *Arabidopsis thaliana* Athranilate Synthase Subunit I in *Escherichia coli,* 106 Plant Physiol. 353–358 (1994).
Brunn, et al., BioChemical Characterization of Auxin Transport Protein Using Phytotropins, Bioregulators for Crop Protection and Pest Control, Chap. 16, 202–211 (Am. Chem. Soc. 1994).
Bernasconi, et al. A Naturally Occurring Point Mutation Confers Broad Range Tolerance to Herbicides that Target Acetolactate Synthase, 270 J. Bio. Chem. 17381–17385 (1995).
Patel, Solubilized Napthylphthalamic Acid Binding Protein, J. Cellular Biochemistry Supplement O (21A) 482 (1995).

METHODS FOR DETECTING ACETOHYDROXYACID SYNTHASE INHIBITORS

Matter enclosed in heavy brackets [ ] appears in the original patent but forms no part of this reissue specification; matter printed in italics indicates the additions made by reissue.

*This is an application for Reissue of U.S. Pat. No. 5,356,789, issued Oct. 18, 1994 on U.S. application Ser. No. 08/068,458 filed May 28, 1993.*

BACKGROUND OF THE INVENTION

The pathway leading to the biosynthesis of branched chain amino acids (valine, leucine and isoleucine) is vital to the survival of plants. This pathway, and the enzymes promoting it, is vulnerable to several classes of highly potent herbicides including imadazolinones, sulfonylureas, sulfonamides and pyrimidyloxybenzoates. Such herbicides act by inhibiting acetohydroxyacid synthase (AHAS), the first enzyme functioning in the pathway.

Recently, weed populations have been discovered which are resistant to AHAS-inhibiting herbicides (D. L. Shaner, Herbicide Resistance in Weeds and Crops, ed. J. C. Caseley, G. W. Cussans and R. K. Atkin (Oxford: Butterworth-Heinemann, 1991), 187–198). These resistant biotypes contain an altered AHAS enzyme which is no longer inhibited by these herbicides. Once such a resistant weed population has developed, the weed management program has to be changed to prevent the propagation of the resistant weed. Therefore, a method to rapidly determine if a weed population has developed resistance to an AHAS-inhibiting herbicide would have great utility and would permit the agriculturalist to adapt his weed management program to control the resistant weed more effectively.

Because several classes of AHAS inhibiting compounds are highly potent herbicides, there is an ongoing search to discover new and more effective AHAS inhibitors. To identify these new inhibitors, assays are used to measure the extent of AHAS inhibition caused by the compounds' use. However, the assays currently employed are often arduous, expensive and/or time-consuming.

It is an object of the present invention to provide a method for determining whether a compound inhibits acetohydroxyacid synthase.

It is also an object of the present invention to provide a method for determining whether a plant is resistant to an acetohydroxyacid synthase inhibitor.

These and other objects of the present invention will become more apparent from the detailed description thereof set forth below.

SUMMARY OF THE INVENTION

The present invention relates to a method for determining whether a compound inhibits acetohydroxyacid synthase (AHAS). In particular, the present invention relates to a method for determining whether a compound inhibits the AHAS enzyme by detecting the presence of and measuring the quantity of its condensation products in a biological system.

The present invention also relates to a novel in vivo method for determining whether a plant is resistant to an AHAS inhibitor. In particular, the present invention relates to a method for determining whether a plant is AHAS-inhibitor resistant by detecting the presence of and measuring the quantity of its condensation products in the biological system and comparing the results to a predetermined standard.

DETAILED DESCRIPTION OF THE INVENTION

Weeds cause tremendous global economic losses by reducing crop yields and lowering crop quality. Several classes of highly potent herbicides effectively control weeds by inhibiting AHAS. Therefore, there is an ongoing search to discover new and more effective AHAS inhibitors. To identify these new inhibitors, assays can be used to measure the products of AHAS activity. However, the assays currently employed are often arduous, expensive and/or time-consuming.

New herbicides have been discovered which inhibit ketolacid reductoisomerase (KARI), the enzyme which immediately follows AHAS in the branched chain amino acid pathway (J. V. Schloss and A. Aulabaugh, Biosynthesis of Branched Chain Amino Acids, ed. Z. Barak, D. M. Chipman and J. V. Schloss (New York: VCH Publishers, 1990), 329–356). Plants treated with these herbicides accumulate acetolactate and acetohydroxybutyrate (AL/AHB), the condensation products of AHAS. The amount of AL/AHB present in the plants can then by measured to determine the extent of inhibition.

Advantageously, the present invention provides a rapid and quantitative method for determining whether a compound inhibits AHAS. The method comprises treating an AHAS inhibitor-susceptible plant or plant part with a biologically active compound and an effective amount of a KARI inhibitor; treating the AHAS inhibitor-susceptible plant or plant part with the KARI inhibitor alone; and measuring the amount of AL and AHB present in the treated plants or plant parts to determine if the amount of AL and AHB present in the plant or plant part treated with the biologically active compound and the KARI inhibitor is less than the amount of AL and AHB present in the plant or plant part treated with the KARI inhibitor alone. Such a result is characteristic of an AHAS inhibiting compound.

Advantageously, the present invention also provides a rapid and quantitative method for determining whether a plant is resistant to an AHAS inhibitor. This method comprises treating a plant or a part of the plant with an effective amount of an AHAS inhibitor and an effective amount of a KARI inhibitor; treating the plant or plant part with an effective amount of the KARI inhibitor alone; and measuring the amount of AL and AHB present in the treated plants or plant parts to determine if the amount of AL and AHB present in the plant or plant part treated with the AHAS inhibitor and the KARI inhibitor correlates with a predetermined AHAS-inhibitor resistance standard. For example, where an effective amount of an AHAS inhibitor and an effective amount of a KARI inhibitor produce a result of at least about 15% of the amount of AL and AHB present in the plant or plant part treated with the KARI inhibitor alone, the plant is essentially AHAS inhibitor resistant. It has been discovered that heterozygous resistant plants treated with an AHAS inhibitor and a KARI inhibitor have about 15% to 50% of the amount of AL and AHB present in the KARI inhibitor-treated plants, and homozygous resistant plants treated with an AHAS inhibitor and a KARI inhibitor have more than 50% of the amount of AL and AHB present in the KARI inhibitor treated plants.

Advantageously, the present invention may be used to determine if weeds are resistant to AHAS inhibitors.

Because of the rapidity of the invention methods, critical decisions can be made on how to treat uncontrolled weeds after AHAS inhibitor applications.

Beneficially, the methods of the present invention can be used in the field or laboratory with minimal equipment. And the methods of this invention are more economical and significantly less time-consuming than the enzyme extraction and green house spray procedures currently employed.

KARI inhibitors which are suitable for use in the methods of the present invention include (dimethylphosphinyl) glycolic acid; 2-(dimethylphosphinoyl)-2-hydroxyacetic acid; sodium N-hydroxy-N-alkyloxamates and sodium N-hydroxy-N-aralkyloxamates. For the N-hydroxy-N-alkyloxamates, the alkyl group is preferably $C_1$–$C_6$ alkyl or $C_3$–$C_7$ cycloalkyl, most preferably isopropyl. A preferred aralkyl group is benzyl.

AHAS inhibitors which are suitable for use in the method used to detect resistance include a) imidazolinone inhibitors such as 5-ethyl-2-(4-isopropyl-4-methyl-5-oxo-2-imidazolin-2-yl) nicotinic acid (imazethapyr);

2-(4-isopropyl-4-methyl-5-oxo-2-imidazolin-2-yl)-3-quinolinecarboxylic acid (imazaquin);

isopropylammonium 2-(4-isopropyl-4-methyl-5-oxo-2-imidazolin-2-yl)nicotinate (imazapyr);

methyl 2-(4-isopropyl-4-methyl-5-oxo-2-imidazolin-2-yl) nicotinate; and 2-(4-isopropyl-4-methyl-5-oxo-2-imidazolin-2-yl)-5-methylnicotinic acid;

b) sulfonylurea inhibitors such as 1-(2-chlorophenylsulfonyl)-3-(4-methoxy-6-methyl-1,3,5-triazin-2-yl)urea (chlorsulfuron);

methyl 2-[3-(4,6-dimethylpyrimidin-2-yl)ureidosulfonyl] benzoate (sulfometuron-methyl); and methyl o-{{3-[4,6-bis(difluoromethoxy)-2-pyrimidinyl] ureido}sulfonyl}benzoate;

c) sulfonamide inhibitors such as

N-(2,6-difluorophenyl)-5-methyl-1,2,4-triazolo[1,5-a] pyrimidine-2-sulfonamide (flumetsulam); and N-(2,6-dichlorophenyl)-5-methyl-1,2,4-triazolo[1,5-a] pyrimidine-2-sulfonamide; and d) pyrimidyloxybenzoate inhibitors such as o-[(4,6-dimethoxy-2-pyrimidinyl)oxy]benzoic acid.

Plant species suitable for use in the methods of the present invention include monocotyledonous plant species such as Johnsongrass, blackgrass and corn, and dicotyledonous plant species such as pigweed, morning glory, chickweed, sunflower, tobacco and lima bean. Plant parts suitable for use in the methods of the invention include young rapidly growing tissue, such as meristematic tissue, with young rapidly growing shoots, leaves, roots and flower buds being preferred.

In the methods of the present invention, the plants or plant parts are preferably treated with an effective amount of an inhibitor or test compound. One of ordinary skill in the art would be able to determine the effective amount of any particular test compound by routine experimentation. For example, about a 1 μM to 1,000 μM, more preferably about 5 μM to 500 μM, most preferably about 10 μM to 100 μM solution of the test compound should be employed, depending on the potency. The solution containing the test compound may be combined with a 1 μM to 1,000 μM solution, preferably about 5 μM to 500 μM, most preferably about 10 μM to 100 μM, of the KARI inhibitor; and/or a 1 μM to 1,000 μM solution, preferably about 5 μM to 500 μM, most preferably about 10 μM to 100 μM, of the AHAS inhibitor. Of course higher concentrations would be similarly effective but may be wasteful and are usually not necessary.

The amount of AL and AHB present in the treated plants and plant parts may be determined according to known procedures in the art such as the method of Westerfeld (J. Biol. Chem. 161, 495–502 (1945)) or gas liquid chromatography.

To determine the amount of AL and AHB present in a plant or plant part according to the method of Westerfeld, the AL and AHB present in the plant or plant part is extracted into water; the water extract is treated with sulfuric acid; the acidified water extract solution is treated with a 0.5% creatine solution and a 5% a-naphthol in sodium hydroxide solution; and the color of the resulting solution is measured to determine the amount of AL and AHB present in the treated plant or plant part.

In order to facilitate a further understanding of the invention, the following examples are presented to illustrate more specific details thereof. The invention is not to be limited thereby as the full scope of the invention is defined in the claims.

EXAMPLE 1

Evaluation of In Vivo Inhibition of Acetohydroxyacid Synthase

Plant Material

Corn (Zea mays) (Pioneer var. 3475) and sunflower (Helianthus annuus) (Dahlgran var. DO-164) seeds are germinated and grown for 6 days in cylinders of germination paper that are kept moist by standing the cylinders in distilled water in a 1 L beaker covered with a perforated plastic bag. Seedlings are transferred to 120 mL plastic containers and grown hydroponically in a modified nutrient solution. All plants are grown in a growth chamber (13 h photoperiod; 28°/22° C.; 300 μE/m$^2$/sec). Corn is treated when the fourth leaf is just emerging from the whorl and sunflowers when the third leaf is emerging. Sulfonylurea-resistant and sensitive chickweed (Stellaria media) are grown from seed in the greenhouse until the plants reach the 2 to 4 leaf stage.

Treatments

Stock solutions of 10 μM technical (dimethylphosphinyl) glycolic acid are made by dissolving 1.52 mg/mL in water and are kept frozen until use. Solutions of different concentrations are made by dilution from this stock solution. Ten μM stock solutions of imazaquin and sulfometuron-methyl are made by dissolving 3.11 and 3.64 mg/mL of technical material, respectively, in a suitable organic solvent, such as acetone or tetrahydrofuran, and dilutions made from these stock solutions. Technical grade amino acids are dissolved directly in application solutions to the desired final concentrations.

In excised shoot (plant part) experiments, shoots are cut free from the roots under degassed water and the excised shoots are placed in vials containing the treatment solutions. At harvest, plants are weighed, cut up, and 1 or 2 g samples are frozen immediately in liquid nitrogen and kept in a −20° C. freezer until analysis.

In the experiment with sulfonylurea-resistant Stellaria media, plants are sprayed with one of the following treatments: 250 g/ha (dimethylphosphinyl)glycolic acid; 250 g/ha imazapyr; 10 g/ha chlorsulfuron; 250 g/ha (dimethylphosphinyl)glycolic acid plus 250 g/ha imazapyr; and 250 g/ha (dimethylphosphinyl)glycolic acid plus 20 g/ha chlorsulfuron; with a moving belt sprayer in a spray volume of 400 L/ha. Plants are kept in a greenhouse until the tissue is extracted to measure AL and AHB levels.

Extraction and Assay Procedures

Plant tissue is pulverized in liquid nitrogen with sand and then ground in ice cold 100 mM phosphate buffer, pH 7.5 (2 mL/g). The mixture is strained through several layers of cheesecloth into a 50 mL centrifuge tube, centrifuged at 24000 g for 15 minutes and the supernatant collected for analysis.

A portion of the supernatant is assayed directly for acetoin and another portion is acidified to 1% $H_2SO_4$ (v/v) and heated for 15 minutes at 60° C. to decarboxylate the AL and AHB. The resulting products are assayed using the method of Westerfeld and the combined product concentration is measured. There is no Westerfeld-positive product in untreated tissue based on differences between extracts before and after acidification. Because of this, the $OD_{520}$ of extracts from untreated tissue is used to correct for background color.

Results

Concentrations of (dimethylphosphinyl)glycolic acid above 1 μM cause an accumulation of AL and AHB in excised corn shoots within 8 hours after application (Table I). Maximum levels appear to accumulate in plants treated with 10 μM to 100 μM solutions of (dimethylphosphinyl) glycolic acid. A time course of this accumulation in excised corn shoots shows that a maximum level is reached by 4 hours after application (Table II). This accumulation can be completely prevented by simultaneously treating the shoots with a 10 μM solution of imazaquin. (Dimethylphosphinyl) glycolic acid causes an accumulation of AL and AHB in excised sunflower shoots which can be prevented by imazaquin treatment (Table III).

Other AHAS inhibitors such as sulfometuron-methyl in the presence of the amino acids valine and leucine (and isoleucine) also prevent the accumulation of AL and AHB caused by (dimethylphosphinyl)glycolic acid (Table IV).

The interaction between (dimethylphosphinyl)glycolic acid and AHAS inhibitors can also be used to determine if a plant is resistant to the AHAS inhibitors. (Dimethylphosphinyl)glycolic acid causes an accumulation of AL and AHB in chlorsulfuron-resistant S. media. The (dimethylphosphinyl)glycolic acid-induced accumulation of AL and AHB is prevented by imazapyr (Table V).

These results also indicate that this relatively easy method can be used to differentiate between AHAS inhibitor resistant and susceptible biotypes by treating plants with a combination of (dimethylphosphinyl)glycolic acid and different AHAS inhibitors. If the biotype is resistant to the AHAS inhibitor, then it will continue to accumulate AL and AHB in the presence of the inhibitor. These data also show that the interaction between AHAS and KARI inhibitors can be used to study the in vivo inhibition of AHAS by monitoring the buildup of AL and AHB in the plant tissue.

In Tables I–V, the AL/AHB levels are given in terms of the optical density reading at 520 nanometers ($OD_{520}$) per gram of fresh weight.

TABLE I

Effect of different concentrations of (dimethylphosphinyl)glycolic acid on AL and AHB accumulation in excised corn shoots eight hours after application

| Concentration of (Dimethylphosphinyl)-glycolic acid (μM) | AL/AHB Levels |
|---|---|
| 0.1 | 0.0 |
| 0.25 | 0.0 |
| 1 | 1.8 |
| 2.5 | 9.7 |
| 10 | 23.4 |
| 25 | 26.2 |
| 100 | 31.7 |

TABLE II

Time course of AL and AHB accumulation in excised corn shoots

| Treatment | Conc. (μM) | AL/AHB Levels Time after treatment (hours) 2 | 4 | 6 | 8 |
|---|---|---|---|---|---|
| (Dimethylphosphinyl)-glycolic acid | 100 | 6.9 | 9.7 | 14.2 | 14.7 |
| Imazaquin | 10 | 0 | 0 | 0 | 0 |
| Imazaquin + (Dimethylphosphinyl)-glycolic acid | 10 + 100 | 0 | 0 | 0 | 0 |

TABLE III

Effect of (dimethylphosphinyl)glycolic acid alone and in combination with imazaquin on AL and AHB accumulation in excised sunflower shoots

| Treatment | Conc. (μM) | AL/AHB Levels |
|---|---|---|
| Dimethylphosphinyl)-glycolic acid | 100 | 0.3 |
| (Dimethylphosphinyl)-glycolic acid + Imazaquin | 100 + 10 | 0.05 |

TABLE IV

Effect of (dimethylphosphinyl)glycolic acid and various AHAS inhibitors on accumulation of AL and AHB in excised corn shoots

| Treatment | Conc. (μM) | AL/AHB Levels |
|---|---|---|
| (Dimethylphosphinyl)glycolic acid | 100 | 18 |
| (Dimethylphosphinyl)glycolic acid + Valine + Leucine | 100 + 10 + 100 | 1 |
| (Dimethylphosphinyl)glycolic acid + Sulfometuron-methyl | 100 + 1 | 0 |

TABLE V

Effect of (dimethylphosphinyl)glycolic acid alone and in combination with various AHAS inhibitors on AL and AHB accumulation in chlorsulfuron resistant *S. media*

| Treatment | Rate (g/ha) | AL/AHB Levels Hours after treatment 24 | 48 |
|---|---|---|---|
| (Dimethylphosphinyl)glycolic acid | 250 | 25 | 53 |
| Chlorsulfuron | 10 | 0 | 0 |
| Imazapyr | 250 | 0 | 0 |
| (Dimethylphosphinyl)glycolic acid + Chlorsulfuron | 250 + 10 | 5 | 25 |
| (Dimethylphosphinyl)glycolic acid + Imazapyr | 250 + 250 | 0 | 0 |

EXAMPLE 2

Evaluation of In Vivo Inhibition of Acetohydroxyacid Synthase in Excised Lima Bean Shoots Young lima bean shoots with primary leaves that are approximately 30% expanded are excised and the cut stem is placed in a 5 μM imazaquin solution, a 100 μM (dimethylphosphinyl)glycolic acid solution, a 100 μM sodium N-hydroxy-N-isopropyloxamate solution, or a 5 μM imazaquin and 100 μM sodium N-hydroxy-N-isopropyloxamate solution. The excised shoots plus solutions are placed in a lighted growth chamber (28° C.) for 7 hours. After this incubation the primary leaves are harvested, frozen overnight at −20° C. and then extracted in boiling water and the level of AL and AHB measured in the water using the Westerfeld reaction.

As can be seen from the data in Table VI, sodium N-hydroxy-N-isopropyloxamate causes an accumulation of AL and AHB in excised lima bean shoots which can be prevented by imazaquin treatment.

In Table VI, the AL/AHB levels are reported in terms of the optical density reading at 520 nanometers ($OD_{520}$) per gram of fresh weight.

TABLE VI

Effect of sodium N-hydroxy-N-isopropyloxamate alone and in combination with imazaquin on AL and AHB accumulation in excised lima bean shoots

| Treatment | Conc. (μM) | AL/AHB Levels |
|---|---|---|
| Imazaquin | 5 | 0.0 |
| (Dimethylphosphinyl)glycolic acid | 100 | 16.6 |
| Sodium N-hydroxy-N-isopropyl-oxamate | 100 | 13.2 |
| Sodium N-hydroxy-N-isopropyl-oxamate + Imazaquin | 100 + 5 | 2.1 |

EXAMPLE 3

Evaluation of In Vivo Inhibition of Acetohydroxyacid Synthase in Susceptible and Heterozygous-resistant Tobacco Leaf discs (7 mm diameter) are cut from young expanding leaves of imazaquin susceptible and heterozygous-resistant tobacco (Nicotiana tabacum). Fifteen discs from each species are floated on 10 mL of a 5 μM imazaquin solution, a 100 μM (dimethylphosphinyl)glycolic acid solution, a 100 μM sodium N-hydroxy-N-isopropyloxamate solution, a 5 μM imazaquin and 100 μM (dimethylphosphinyl)glycolic acid solution, or a 5 μM imazaquin and 100 μM sodium N-hydroxy-N-isopropyloxamate solution contained in a petri plate. The discs plus solutions are incubated in a lighted growth chamber for [16] *24* hours. Then the discs are harvested, frozen on dry ice and extracted in boiling water. The AL and AHB level in the water is determined using the Westerfeld reaction.

As can be seen from the data in Table VII, (dimethylphosphinyl)glycolic acid and sodium N-hydroxy-N-isopropyloxamate cause an accumulation of AL and AHB in tobacco leaf discs. This accumulation can be prevented in susceptible tobacco by imazaquin treatment. And AL and AHB accumulation in heterozygous-resistant tobacco can be prevented up to 50% by imazaquin treatment.

In Table VII, A designates imazaquin susceptible tobacco and B designates imazaquin heterozygous-resistant tobacco.

In Table VII, the AL/AHB levels are reported in terms of the optical density reading at 520 nanometers ($OD_{520}$) per [gram] *0.1 gram* of fresh weight.

TABLE VII

| Treatment | Conc. (μM) | AL/AHB Levels Tobacco Species A | B |
|---|---|---|---|
| Imazaquin | 5 | 0.0 | 0.0 |
| (Dimethylphosphinyl)glycolic acid | 100 | 2.7 | 2.2 |
| Sodium N-hydroxy-N-isopro-pyloxamate | 100 | 2.1 | 1.8 |
| (Dimethylphosphinyl)-glycolic acid + Imazaquin | 100 + 5 | 0.0 | 1.2 |
| Sodium N-hydroxy-N-isopro-pyloxamate + Imazaquin | 100 + 5 | 0.2 | 1.0 |

EXAMPLE 4

Evaluation of In Vivo Inhibition of Acetohydroxyacid Synthase in Various Weed Species Samples of imazaquin susceptible crabgrass, morning glory and Johnsongrass and imazaquin resistant cocklebur are treated with a 0.2% imazaquin solution, a 0.1% (dimethylphosphinyl)glycolic acid solution or a 0.2% imazaquin and 0.1% (dimethylphosphinyl)glycolic acid solution. Approximately one gram of the material from each of the treatments is placed in a test tube and 5 mL of water is added. The test tubes with the leaf material plus water are heated in a boiling water bath for 15 minutes. Three to 150 μL aliquots of the water extract are placed in separate wells of a 96-well microtiter plate for each treatment. Twenty-five μL of 5% $H_2SO_4$ is added to each well and the plate is heated at 60° C. for 15 minutes. [Seventy-five] *Sixty Two* μL each of 0.5% creatine in water and 5% α-naphthol in 4N NaOH is added to each well and the plate is heated at 60° C. for 15 minutes. The plate is centrifuged for [10] *15* minutes at 3000 g and the $OD_{520}$ is read for each well on a microtiter plate reader. The results are summarized in Table VIII.

As can be seen from the data in Table VIII, (dimethylphosphinyl)glycolic acid causes an accumulation of AL and AHB in various weed species. This accumulation can be prevented in crabgrass, morning glory and Johnsongrass by imazaquin treatment. The accumulation of AL and AHB in the cocklebur plant was reduced by one-half by imazaquin treatment. Therefore, these results indicate that the cocklebur plant is resistant to imazaquin.

In Table VIII, the acetolactate and acetohydroxybutyrate levels are reported in terms of the optical density reading at 520 nanometers ($OD_{520}$) per [gram] *0.15 gram* of fresh weight.

TABLE VIII

| | Acetolactate/Acetohydroxybutyrate Levels Weed Species | | | |
|---|---|---|---|---|
| Treatment | Crabgrass | Morning glory | Johnsongrass | Cocklebur |
| Imazaquin | 0 | 0 | 0 | 0 |
| (Dimethylphosphinyl)glycolic acid | 1.7 | 1.5 | 0.5 | 1.0 |
| (Dimethylphosphinyl)glycolic acid + Imazaquin | 0 | 0 | 0 | 0.5 |

EXAMPLE 5

Evaluation of In Vivo Inhibition of Acetohydroxyacid Synthase in Imazaquin Susceptible and Resistant Cocklebur (Xanthium Strumarium)

Imazaquin susceptible and resistant cocklebur plants are treated in the field with a 0.1% imazaquin solution, a 0.1% (dimethylphosphinyl)glycolic acid solution or a 0.1% imazaquin and 0.1% (dimethylphosphinyl)glycolic acid solution. One or two days after treatment, the young rapidly expanding leaves are collected. Approximately one gram of the leaf material from each of the treatments is placed in a test tube and 5 mL of water is added. The test tubes with the leaf material plus water are heated in a boiling water bath for 15 minutes. Three to 150 μL aliquots of the water extract are placed in separate wells of a 96-well microtiter plate for each treatment. Twenty-five μL of 5% $H_2SO_4$ is added to each well and the plate is heated at 60° C. for 15 minutes. [Seventy-five] *Fifty* μL each of 0.5% creatine in water and *75 μL* 5% α-naphthol in 4N NaOH is added to each well and the plate is heated at 60° C. for 15 minutes. The plate is centrifuged for 10 minutes at 3000 g and the [$OD_{520}$] $OD_{535}$ is read for each well on a microtiter plate reader. The results are summarized in Table IX.

As can be seen from the data in Table IX, (dimethylphosphinyl)glycolic acid causes an accumulation of AL and AHB in both cocklebur plants. This accumulation can be prevented in the imazaquin susceptible cocklebur plant. However, the accumulation of AL and AHB in the other cocklebur plant could not be completely prevented by imazaquin treatment. Therefore, these results indicate that this cocklebur plant is resistant to imazaquin.

TABLE I

| | AL/AHB Levels Cocklebur Plant | |
|---|---|---|
| Treatment | Imazaquin-Susceptible | -Resistant |
| (Dimethylphosphinyl)-glycolic acid | 3.42 | 3.44 |
| (Dimethylphosphinyl)-glycolic acid + Imazaquin | 0.04 | 1.39 |

I claim:

1. An in vivo method for determining whether a compound inhibits acetohydroxyacid synthase which comprises:

(a) treating a first acetohydroxyacid synthase inhibitor-susceptible plant or plant part with an effective amount of the compound and an effective amount of a ketol-acid reductoisomerase inhibitor;

(b) treating a second acetohydroxyacid synthase inhibitor-susceptible plant or plant part from the same population of the same species with the effective amount of the ketol-acid reductiosomerase inhibitor alone; and (c) measuring the amounts of acetolactate and acetohydroxybutyrate present in the treated plants or plant parts to determine if the amount of acetolactate and acetohydroxybutyrate present in (a) is less than the amount of acetolactate and acetohydroxybutyrate present in (b).

2. The method according to claim 1 wherein the ketol-acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.

3. The method according to claim 2 wherein the alkyl component of the N-hydroxy-N-alkyloxamate is selected from $C_1$–$C_6$ alkyl and $C_3$–$C_7$ cycloalkyl.

4. The method according to claim 3 wherein the alkyl component is isopropyl.

5. The method according to claim 2 wherein the aralkyl component is benzyl.

6. The method according to claim 1 wherein the acetohydroxyacid synthase inhibitor susceptible plant is selected from the group consisting of a monocotyledonous plant and a dicotyledonous plant.

7. The method according to claim 1 wherein the plant parts are young rapidly growing tissue.

8. The method according to claim 1 wherein the amount of acetolactate and acetohydroxybutyrate present in the treated plant or plant part is determined by:

(a) extracting the acetolactate and acetohydroxybutyrate present in the treated plant or plant part into water;

(b) treating the water extract with a sulfuric acid solution;

(c) treating the acidified water extract solution from (b) with a 0.5% creatine solution and a 5% α-naphthol in sodium hydroxide solution; and (d) measuring and comparing the color of the product of (c) to a known standard.

9. The method according to claim 1 wherein the plant or plant part is treated with a 1 μM to 1,000 μM solution of the compound and a 1 μM to 1,000 μM solution of the ketol-acid reductoisomerase inhibitor.

10. An in vivo method for determining whether a population of a plant species is resistant to an acetohydroxyacid synthase inhibitor which comprises:

(a) treating a first plant or a part of the plant with an effective amount of the acetohydroxyacid synthase inhibitor and an effective amount of a ketol-acid reductoisomerase inhibitor;

(b) treating a second plant or plant part from the same population of the same species with the effective amount of the ketol-acid reductoisomerase inhibitor alone;

(c) measuring the amounts of acetolactate and acetohydroxybutyrate present in the treated plants or plant parts to determine if the amount of acetolactate and acetohydroxybutyrate present in (a) is at least about 15% of the amount of acetolactate and acetohydroxybutyrate present in (b).

11. The method according to claim 10 wherein the acetohydroxyacid synthase inhibitor is selected from the group consisting of an imidazolinone, a sulfonylurea, a sulfonamide and a pyrimidyloxybenzoate.

12. The method according to claim 11 wherein the imidazolinone is selected from the group consisting of 5-ethyl-2-(4-isopropyl-4-methyl-5-oxo-2-imidazolin-2-yl) nicotinic acid;

2-(4-isopropyl-4-methyl-5-oxo-2-imidazolin-2-yl)-3-quinolinecarboxylic acid;

isopropylammonium 2-(4-isopropyl-4-methyl-5-oxo-2-imidazolin-2-yl)nicotinate;

methyl 2-(4-isopropyl-4-methyl-5-oxo-2-imidazolin-2-yl) nicotinate; and 2-(4-isopropyl-4-methyl-5-oxo-2-imidazolin-2-yl)-5-methylnicotinic acid.

13. The method according to claim 10 wherein the ketol-acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.

14. The method according to claim 13 wherein the alkyl component of the N-hydroxy-N-alkyloxamate is selected from $C_1$–$C_6$ alkyl and $C_3$–$C_7$ cycloalkyl.

15. The method according to claim 14 wherein the alkyl component is isopropyl.

16. The method according to claim 13 wherein the aralkyl component is benzyl.

17. The method according to claim 10 wherein the plant parts are young rapidly growing tissue.

18. The method according to claim 10 wherein the amount of acetolactate and acetohydroxybutyrate present in the treated plant or plant part is determined by (a) extracting the acetolactate and acetohydroxybutyrate present in the plant or plant part into water;

(b) treating the water extract with a sulfuric acid solution;

(c) treating the acidified water extract solution from (b) with a 0.5% creatine solution and a 5% α-naphthol in sodium hydroxide solution; and (d) measuring and comparing the color of the product of (c) to a known standard.

19. The method according to claim 10 wherein the plant or plant part is treated with a 1 μM to 1,000 μM solution of the acetohydroxyacid synthase inhibitor and a 1 μM to 1,000 μM solution of the ketol-acid reductoisomerase inhibitor.

*20. A method for determining whether a material to be tested is capable of inhibiting acetolactate synthesis in a given plant tissue sample containing living cells which comprises the steps of:*

*(a) combining in an aqueous medium the plant tissue sample, an effective amount of the material, and an effective amount of an inhibitor of keto acid reductoisomerase, so that acetolactate will accumulate in the mixture unless the material inhibits acetolactate synthesis; and*

*(b) detecting accumulation of acetolactate.*

*21. The method according to claim 20 wherein the keto acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.*

*22. The method according to claim 21 wherein the alkyl component of the N-hydroxy-N-alkyoxamate is selected from $C_1$–$C_6$ alkyl and $C_3$–$C_7$ cycloalkyl.*

*23. The method according to claim 22 wherein the alkyl component is isopropyl.*

*24. The method according to claim 21 wherein the aralkyl component is benzyl.*

*25. The method according to claim 20 wherein the given plant tissue sample is selected from the group consisting of a monocotyledonous plant and a dicotyledonous plant.*

*26. The method according to claim 20 wherein the given plant tissue sample is young rapidly growing tissue.*

*27. The method according to claim 20 wherein step (b), detecting accumulation of acetolactate, comprises the steps of:*

*(c) extracting the acetolactate present in the given plant tissue sample into water;*

*(d) treating the water extract with a sulfuric acid solution;*

*(e) treating the acidified water extract solution from (d) with a 0.5% creatine solution and a 5% α-naphthol in sodium hydroxide solution; and*

*(f) measuring and comparing the color of the product of (e) to a known standard.*

*28. The method according to claim 20 wherein the given plant tissue sample is treated with a 1 μM to 1,000 μM solution of the material and a 1 μM to 1,000 μM solution of the keto acid reductoisomerase inhibitor.*

*29. A method of claim 20 wherein step (b), detecting accumulation of acetolactate, comprises the steps of:*

*(c) allowing time for acetolactate to accumulate;*

*(d) rupturing the cells;*

*(e) acidifying said mixture to convert any accumulated acetolactate to acetoin, and*

*(f) colorimetrically detecting the presence of acetoin in the mixture.*

*30. The method of claim 29 wherein step (f) comprises the step of adding an effective amount of a compound containing the guanidino group, 1-naphthol, and base to the mixture.*

*31. The method of claim 30 wherein the compound containing the guanidino group is creatine.*

*32. A method for determining whether a given plant is resistant to a herbicide known to have inhibition of acetolactate synthase as its mode of action, which comprises:*

*(a) combining in an aqueous medium a fresh sample of tissue from said plant, an effective amount of said herbicide, and an effective amount of a keto acid reductoisomerase inhibitor; and*

*(b) detecting the accumulation of acetolactate.*

*33. The method according to claim 32 wherein the herbicide is an acetohydroxyacid synthase inhibitor selected from the group consisting of an imidazolinone, a sulfonylurea, a sulfonamide and a pyrimidyloxybenzoate.*

*34. The method according to claim 33 wherein the imidazolinone is selected from the group consisting of*

*5-ethyl-2-(4-isopropyl-4-methyl-5-oxo-2-imidazolin-2-yl) nicotinic acid;*

*2-(4-isopropyl-4-methyl-5-oxo-2-imidazolin-2-yl)-3-quinolinecarboxylic acid;*

*isopropylammonium 2-(4-isopropyl-4-methyl-5-oxo-2-imidazolin-2-yl)nicotinate;*

*methyl 2-(4-isopropyl-4-methyl-5-oxo-2-imidazolin-2-yl) nicotinate; and*

*2-(4-isopropyl-4-methyl-5-oxo-2-imidazolin-2-yl)-5-methylnicotinic acid.*

*35. The method according to claim 32 wherein the keto acid reductoisomerase inhibitor is selected from the group consisting of (dimethylphosphinyl)glycolic acid, 2-(dimethylphosphinoyl)-2-hydroxyacetic acid, sodium N-hydroxy-N-alkyloxamate and sodium N-hydroxy-N-aralkyloxamate.*

*36. The method according to claim 35 wherein the alkyl component of the N-hydroxy-N-alkyloxamate is selected from $C_1$–$C_6$ alkyl and $C_3$–$C_7$ cycloalkyl.*

*37. The method according to claim 35 wherein the alkyl component is isopropyl.*

*38. The method according to claim 35 wherein the aralkyl component is benzyl.*

*39. The method according to claim 32 wherein the given plant tissue sample is young rapidly growing tissue.*

*40. The method according to claim 32 wherein step (b), detecting the accumulation of acetolactate, comprises the steps of:*

*(c) extracting the acetolactate present in the given plant tissue sample into water;*

*(d) treating the water extract with a sulfuric acid solution;*

*(e) treating the acidified water extract solution from (d) with a 0.5% creatine solution and a 5% α-naphthol in sodium hydroxide solution; and*

*(f) measuring and comparing the color of the product of (e) to a known standard.*

*41. The method according to claim 32 wherein the given plant tissue sample is treated with a 1 μM to 1,000 μM solution of the acetohydroxyacid synthase inhibitor and 1 μM to 1,000 μM solution of the keto acid reductoisomerase inhibitor.*

*42. The method of claim 32 wherein said herbicide is known to have inhibition of acetolactate synthase as its mode of action.*

*43. The method of claim 32 wherein the herbicide is selected from the group consisting of flumetsulam, imazaquin, chlorsulfuron, sulfometuron-methyl, imazapyr, and imazethapyr.*

*44. The method of claim 32 wherein step (b), detecting the accumulation of acetolactate, comprises the steps of:*

*(c) rupturing the cells of said plant tissue sample;*

*(d) acidifying said mixture, formed by the combining step (a), to convert any accumulated acetolactate to acetoin; and*

*(e) adding effective amounts of a compound containing the guanidino group, 1-naphthol, and base to the mixture, so that the color of the resulting mixture indicates whether acetolactate synthesis was inhibited.*

*45. The method of claim 44 wherein the compound containing the guanidino group is creatine.*

* * * * *